United States Patent
Loynes

(10) Patent No.: US 6,612,839 B2
(45) Date of Patent: Sep. 2, 2003

(54) GINGIVAL RETRACTOR

(76) Inventor: Murgesh J. Loynes, 861 S. Greenbrier St., Apt. #38, Arlington, VA (US) 22204

(*) Notice: Subject to any disclaimer, the term of this patent is extended or adjusted under 35 U.S.C. 154(b) by 0 days.

(21) Appl. No.: 10/109,267

(22) Filed: Mar. 28, 2002

(65) Prior Publication Data

US 2002/0146664 A1 Oct. 10, 2002

Related U.S. Application Data

(60) Provisional application No. 60/281,252, filed on Apr. 4, 2001.

(51) Int. Cl.[7] .............................................. A61C 5/14
(52) U.S. Cl. ...................................................... 433/136
(58) Field of Search ........................... 433/40, 39, 148, 433/149, 136, 138, 139

(56) References Cited

U.S. PATENT DOCUMENTS

| | | | | |
|---|---|---|---|---|
| 2,749,616 A | * | 6/1956 | Curry | 433/39 |
| 4,465,462 A | * | 8/1984 | Ticknor | 43/136 |
| 4,871,311 A | * | 10/1989 | Hagne | 433/136 |
| 5,114,341 A | * | 5/1992 | Kassel | 433/39 |

* cited by examiner

Primary Examiner—Cary E. O'Connor
(74) Attorney, Agent, or Firm—Gunn, Lee & Hanor P.C.; Michelle Evans

(57) ABSTRACT

A gingival retractor for placement at or into the gingival crevice surrounding a tooth used to deflect gingival tissues away from the tooth to aid in dental procedures. The retractor includes a flexible brace. This brace supports prongs or legs that extend toward the root of the tooth. One or more retractors can be placed into the gingival crevice as needed given the particular tooth and procedure involved.

12 Claims, 3 Drawing Sheets

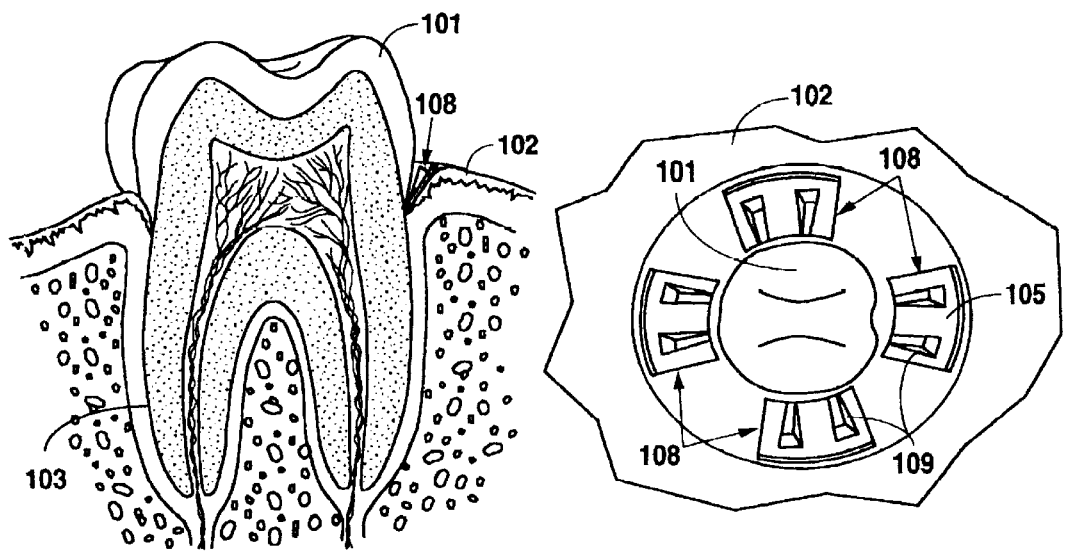
Fig. 2a
Fig. 2e
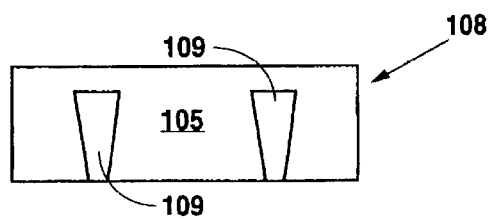
Fig. 2b
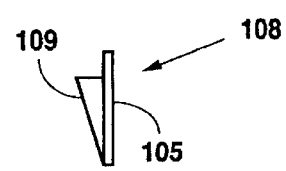
Fig. 2c
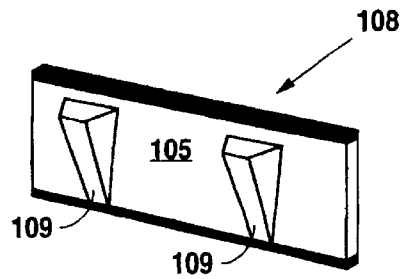
Fig. 2d

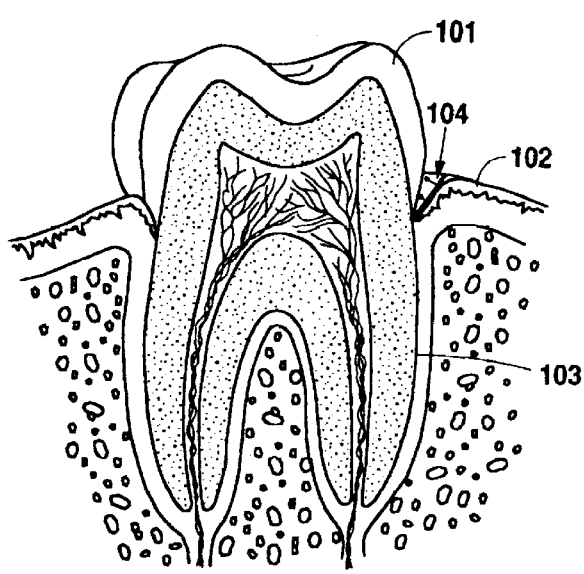
Fig. 3a
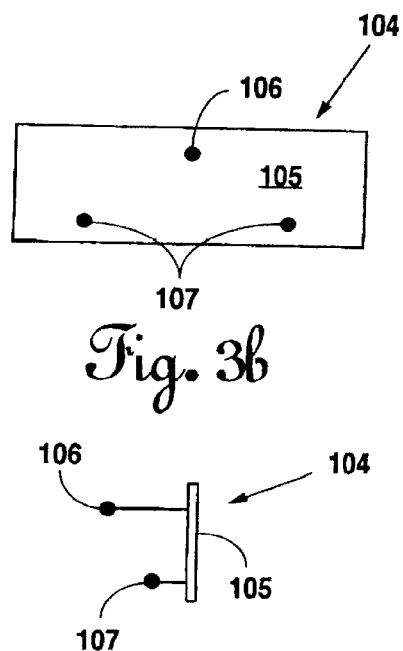
Fig. 3b
Fig. 3c
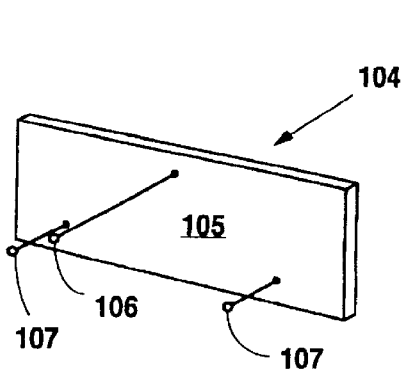
Fig. 3d
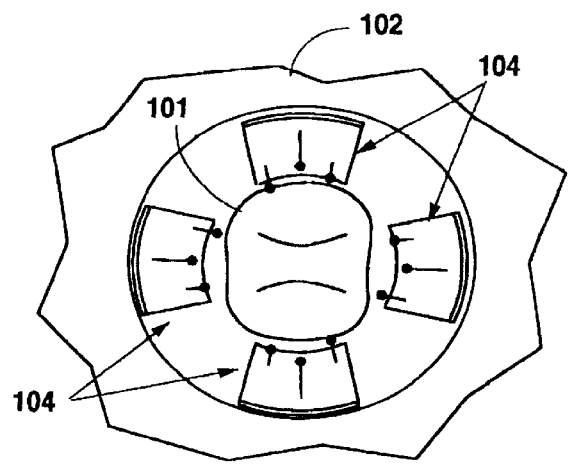
Fig. 3e

GINGIVAL RETRACTOR

The present application claims priority from U.S. Provisional Patent Application Ser. No. 60/281,252 filed Apr. 4, 2001.

BACKGROUND OF THE INVENTION

1. Field of The Invention

Applicant's invention relates to a gingival retractor for placement at or into the gingival crevice surrounding a tooth and used to deflect gingival tissues away from the tooth to aid in dental procedures. More particularly, the present invention relates to a gingival retractor that can be used in dental procedures without the incorporation of dental retraction cords thus minimizing or eliminating trauma to the surrounding gingival tissue.

2. Background Information

Crowns and bridges are common dental procedures. With these dental procedures, the upper portion of a tooth is prepped down into shape as an abutment and replaced by a prosthetic crown. The tooth is typically prepped to a margin being at or slightly below the gum line and defined by the surrounding gingival tissue. A moldable impression material such as a vinyl-based elastomer or polyvinylsiloxane (PVS) is placed over the tooth and allowed to cure, resulting in an impression of the patient's teeth. This impression is then used by a dental laboratory to produce a prosthetic crown for the patient. The prosthetic crown is then permanently cemented onto the prepared tooth.

The fit of the crown at the margin is critical in order to maintain prolonged life of the prepared tooth in the margin area without decay. In order to ensure that the crown will fit into the margin area to maintain the life of the prepared tooth, it is important that the impression material be able to flow somewhat below the margin of the prepared tooth. Unfortunately, since the margin is at or below the gum line, gingival tissue without insertion of any devices typically blocks the flow of impression material below the gum line.

Currently in order to solve this problem retraction cords have been used to temporarily deflect gingival tissue away from the tooth to expose the margin. In such a situation, prior to tooth preparation a flexible retraction cord is packed into the gingival crevice surrounding the prepared tooth. This cord is placed below the gum line and is used to separate the gingival tissue from the tooth in the margin area. Such packing of the cord almost always induces bleeding and gingival tissue tearing in the patient's mouth. The retraction cord is then removed immediately prior to making the impression. In theory, this permits the impression material to flow into the margin area for reproduction. In practice however, the insertion of the retraction cord into the gingival tissue causes some amount of bleeding that impression is rather difficult. Furthermore, since the retraction cord has to be removed before the impression can be made, the gingival tissue often relapse back to its original formation, particularly with healthy gum tissue, thus defeating the purpose of deflecting the gum tissue.

There exists a need in the dental industry for a gingival retractor that does not cause such excess damage to the surrounding gingival tissue and can be left in place without trauma while the dental impression is made so as to prevent the gum tissue from relapsing back into place. The present invention fulfills this need and provides additional advantages. The gingival retractor of the present invention when used for final impression for dental procedures provides a non-contaminated, safe, clear and clean working area to accurately establish marginal integrity of the prep. In addition, it is easier to place since the present invention can be used in multiple pieces which can be placed at the sides of the tooth one at a time rather than all at once which is the case with the retraction cord. Furthermore, there is less extension of pocket depth with the present retractor especially when compared to the double cord system which could extend pocket depth up to 2 mm beyond the original pocket depth of 1.8–2.0 mm. Also, there is less contamination and bleeding can be easily controlled with the present invention unlike the retraction cord which after removal causes the tissue to bleed and causes contamination of the margins. In addition, there is no tissue relapse because the present invention is left in place until after the impression is taken unlike the retraction cord which when taken out of the gingival crevice tends to relapse and interfere with the margin. Also, the present invention will adapt well in the sulcus, so it is good for tissue management because the present invention will not require a repetitious placement like the cord and the tissue will not dry out as with the cord. Furthermore, the present invention can be modified within obvious parameters to accommodate different sizes and shapes of teeth. In addition, the present invention can be modified to adapt to the gingival crevice or to the tooth which is not possible with the cord.

SUMMARY OF THE INVENTION

It is an object of the present invention to provide a novel gingival retractor.

Still another object of the present invention is to provide a novel gingival retractor that incorporates a flexible brace.

It is yet another object of the present invention to provide a novel gingival retractor that incorporates prongs or legs extending from the flexible brace.

Yet another object of the present invention is to provide a novel gingival retractor that incorporates a brace cushion.

In satisfaction of these and related objectives, Applicant's present invention provides a gingival retractor for use in dental procedures. This gingival retractor is for placement at or into the gingival crevice surrounding a tooth and used to deflect gingival tissues away from the tooth to aid in dental procedures. Applicant's invention permits its practitioner to perform dental procedures on patients without the use of retraction cords.

BRIEF DESCRIPTION OF THE DRAWINGS

FIG. 2a is a cross section of a tooth illustrating placement of the preferred embodiment of the gingival retractor of the present invention.

FIG. 2b is a front view of the preferred embodiment of the gingival retractor of the present invention.

FIG. 2c is a side view of the preferred embodiment of the gingival retractor of the present invention.

FIG. 2d is a perspective view of the preferred embodiment of the gingival retractor of the present invention.

FIG. 2e is a top view of a tooth showing placement of the preferred embodiment of the gingival retractor of the present invention.

FIG. 3a is a cross section of a tooth illustrating the placement of the second embodiment of the gingival retractor of the present invention.

FIG. 3b is a front view of the second embodiment of the gingival retractor of the present invention.

FIG. 3c is a side view of the second embodiment of the gingival retractor of the present invention.

FIG. 3d is a perspective view of the second embodiment of the gingival retractor of the present invention.

FIG. 3e is a top view of a tooth showing placement of the second embodiment of the gingival retractor of the present invention.

DETAILED DESCRIPTION

Figure 1:
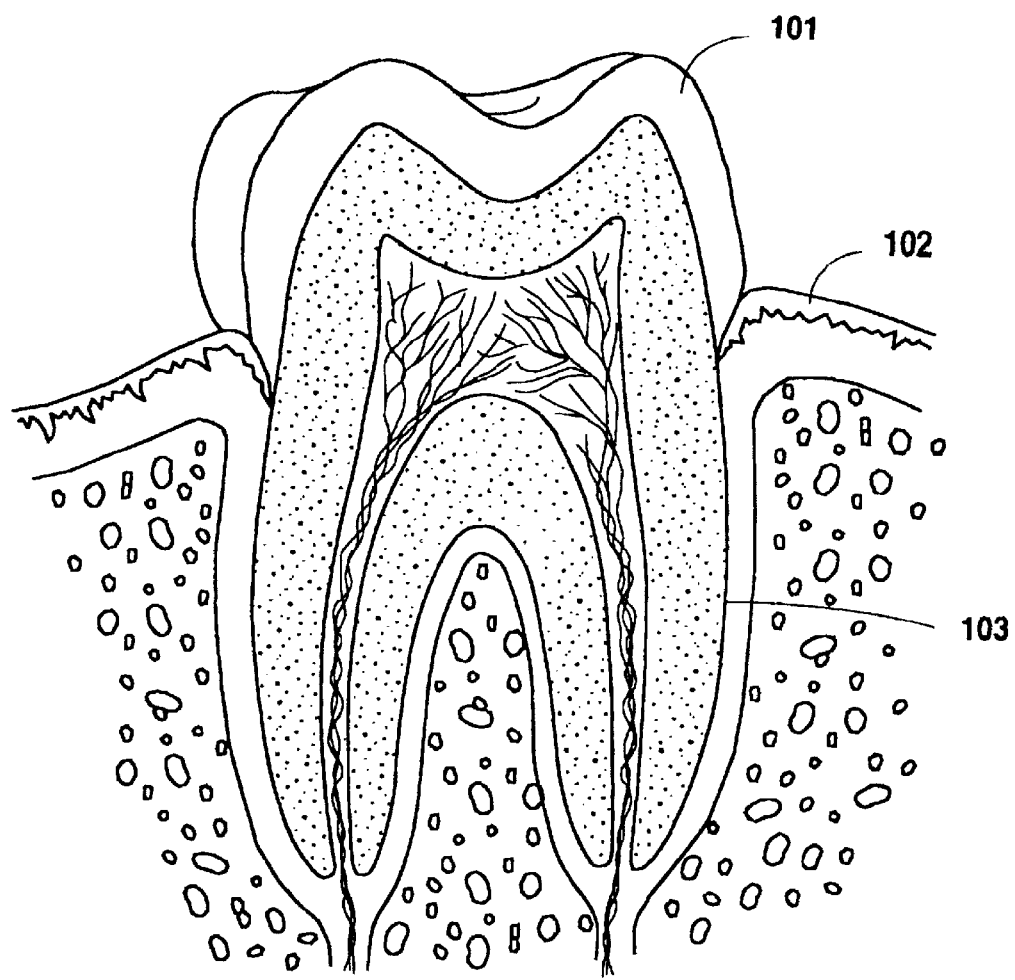
FIG. 1 is a cross section of a tooth.

FIG. 1 illustrates a cross section of a tooth 101. The gingival tissue 102 and periodontal membrane 103 are shown. The gingival tissue 102 typically fits closely around the tooth 101 to define a gingival crest at the gum line. From the gingival crest, the tissue descends alongside the tooth to define a shallow gingival crevice or sulcus. This sulcus typically has a depth on the order of 1.8 to 2.0 mm. The base of the sulcus includes the periodontal tissue 103 secured to the tooth 101.

In FIG. 2a a cross section of a tooth 101 illustrating placement of the preferred embodiment 108 of the gingival retractor of the present invention is shown. Gingival tissue 102 is present deflected from tooth 101. Inserted between tooth 101 and gingival tissue 102 is preferred embodiment 108 of the gingival retractor of the present invention. A front, side, and perspective view of the preferred embodiment of the present invention are illustrated in FIGS. 2b, 2c and 2d respectively.

The preferred embodiment 108 of the gingival retractor of the present invention includes a flexible brace 105, the back surface of which is also designed to abut the gingival tissue 102. Flexible brace 105 is preferably no more than 2 mm tall so as to not allow too much penetration into the gum which would cause trauma to and bleeding of the gingival tissue 102. The length and thickness of the flexible brace 105 can vary, but must be appropriate for the application. The flexible brace 105 can be made from any moldable material such as wood, metal, or plastic. On the front surface of the flexible brace 105 are two prongs 109 spaced apart, with the small portion of the prongs 109 being at the lower portion of the flexible brace 105, or the sucular end, and the larger portion of the prongs 109 being located at the upper portion of the flexible brace 105, or occlusal end. The sucular end of the prongs 109 is in the range of 0 mm to 0.5 mm and the occlusal end of the prongs 109 is in the range of 0.8 mm to 1.0 mm. The central portion of prongs 109 slopes from the sucular end to the occlusal end accordingly. The number of prongs 109 may vary based on the length of flexible brace 105 that is used. A pad or cushion (not shown) can be attached at the bottom of flexible brace 105 to support the tissue from damage. This pad can consist of a thin absorbent pad or sponge.

FIG. 2e shows a top view of a tooth 101 with placement of the preferred embodiment 108 of the gingival retractor of the present invention. Multiple gingival retractors can be used to surround a tooth 101 in preparation for any number of dental procedures. The number of gingival retractors will typically be four for a typical tooth, but can vary based on the size and shape of the tooth on which the dental procedure is to be performed and the size of the flexible brace 105 that is initially used. The goal of insertion of the preferred embodiment 108 of the present invention is to create a clear zone around the tooth 101 to allow access to the margin for the designated dental procedure.

FIG. 3a is a cross section of a tooth 101 illustrating the placement of the second embodiment 104 of the gingival retractor of the present invention. Again the gingival tissue 102 is present, but is illustrated being deflected away from the tooth 101. Shown inserted in between the tooth 101 and the gingival tissue 102 is the second embodiment 104 of the gingival retractor of the present invention. A front, side, and perspective view of the second embodiment 104 of the gingival retractor of the present invention are shown in more detail in FIGS. 3b, 3c and 3d respectively.

The second embodiment 104 of the gingival retractor includes the same flexible brace 105, the back surface of which is designed to abut the gingival tissue 102. Flexible brace 105 is preferably no more than 2 mm tall so as to not allow too much penetration into the gum which would cause trauma to and bleeding of the gingival tissue 102. The length and thickness of the flexible brace 105 can vary, but must be appropriate for the application. The flexible brace 105 can be made from any moldable material such as wood, metal, or plastic. On the front surface of flexible brace 105 are first legs 107 and second leg 106. First legs 107 are located on the lower portion, or sulcular end, of the front surface of flexible brace 105 and second leg 106 is located at the upper portion, or occlusal end, of the front surface of flexible brace 105. First legs 107 are shorter in comparison to second leg 106 with first legs 107 being in the range of 0.3 to 0.5 mm and second leg 102 being in the range of about 0.8 to 1.0 mm. Both first legs 107 and second leg 106 have smoothed tips which are desired to help prevent damage to tooth 101 and gingival tissue 102 upon insertion. The number of first legs 107 and second leg 106 may vary based on the length of flexible brace 105 that is used.

When the second embodiment 104 of the gingival retractor is inserted between the tooth 101 and gingival tissue 102, the sulcular end of the flexible brace 105 precedes the occlusal end. The size of first legs 107 and second leg 106 protruding toward the root of the tooth 101 is actually the measurement of the gingival tissue 102 being displaced from the tooth 101 creating a clear and visible work area to achieve the desired purpose. A pad or cushion (not shown) can be attached at the bottom of flexible brace 105 to support the tissue from damage. This pad can consist of a thin absorbent pad or sponge.

A top view of a tooth 101 showing placement of the second embodiment 104 of the gingival retractor of the present invention is shown in FIG. 3e. Multiple gingival retractors can be used to surround a tooth 101 in preparation for any number of dental procedures. The number of gingival retractors will typically be four for a typical tooth, but can vary based on the size and shape of the tooth on which the dental procedure is to be performed and the size of the flexible brace 105 that is initially used. The goal of insertion of the second embodiment 104 of the present invention is to create a clear zone around the tooth 101 to allow access to the margin for the designated dental procedure.

In alternate embodiments (not shown) the upper portion of flexible brace 105 can be curved to adapt to the gingival contour. Other embodiments include constructing the invention as one piece which can include a wedge or other similar design with the sulcal end being 0.3 mm to 0.5 mm and the occlusal end being 0.8 mm to 1.0 mm.

There are specific directions for placement of the gingival retractor of the present invention. First, the sulcal area must be cleaned using water and air and any visible debris removed. Next, one gingival retractor is placed at a time using cotton forceps in each area of the tooth, for example, the buccal, mesial, lingual and distal areas. The gingival retractor of the present invention is then placed at or below the margins. Once secure, water and air are gently blown into the area to clear any debris. Once the tissue is reflected with the gingival retractor, the next step in the designated dental procedure occurs, for example, impressions, isolations of subgingival restorations, marginal access for provisional or prep, or subgingival prep for a vaneer.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A gingival retractor comprising:
   a flexible brace having a sulcal end and an occlusal end; and
   extensions supported by said flexible brace defining a generally angular profile from said sulcal end to said occlusal end of said flexible brace, said flexible brace coupled with said extensions having a narrow profile of 1.0 mm or less in width.

2. The gingival retractor of claim 1 wherein said extensions are composed of prongs angled out from said sulcal end to said occlusal end on said flexible brace to form said generally angular profile.

3. The gingival retractor of claim 2 wherein said sulcal end of said prongs is in the range of 0 mm to 0.5 mm.

4. The gingival retractor of claim 3 wherein said occlusal end of said prongs is in the range of 0.8 mm to 1.0 mm.

5. The gingival retractor of claim 1 wherein said extensions are composed of legs placed at said sulcal end and said occlusal end of said flexible brace of different lengths to form said generally angular profile.

6. The gingival retractor of claim 5 wherein said legs further comprise first legs at said sulcal end and second leg at said occlusal end.

7. The gingival retractor of claim 6 wherein said first legs are about 0.3 mm to 0.5 mm long.

8. The gingival retractor of claim 7 wherein said second leg is about 0.8 mm to 1.0 mm long.

9. The gingival retractor of claim 1 wherein said flexible brace is no more than 2 mm in height.

10. The gingival retractor of claim 1 further comprising a pad attached to said flexible brace.

11. The gingival retractor of claim 1 wherein said occlusal end is curved to adapt to the gingival contour.

12. The gingival retractor of claim 1 wherein said flexible brace is composed of a moldable material selected from the group consisting of plastic, metal, and wood.

* * * * *